United States Patent [19]

Porter

[11] 4,377,976
[45] Mar. 29, 1983

[54] ART AID DEVICES

[76] Inventor: Elizabeth J. Porter, 1119 9th Ave., Belle Fourche, S. Dak. 57717

[21] Appl. No.: 176,097

[22] Filed: Aug. 7, 1980

[51] Int. Cl.³ .............................................. A47B 41/06
[52] U.S. Cl. ....................................... 108/28; 108/50; 248/118; 248/441 C
[58] Field of Search .......... 40/606; 248/441 R, 441 B, 248/441 C, 451, 452, 453, 458, 459, 118; 434/85, 87, 428; 108/28, 50

[56] References Cited

U.S. PATENT DOCUMENTS

| | | | |
|---|---|---|---|
| 1,518,680 | 12/1924 | Arnot | 434/85 |
| 2,003,482 | 6/1935 | Fancher | 248/441 B |
| 3,416,764 | 12/1968 | Bier | 248/441 B |
| 3,972,133 | 8/1976 | Parshall | 248/441 R |
| 3,975,850 | 8/1976 | Giaume | 40/606 |

FOREIGN PATENT DOCUMENTS

544756 2/1932 Fed. Rep. of Germany ........ 40/606
2832431 2/1980 Fed. Rep. of Germany ........ 40/606

*Primary Examiner*—Richard R. Stearns
*Attorney, Agent, or Firm*—Ancel W. Lewis, Jr.

[57] ABSTRACT

The problem of limited arm and wrist motor capabilities in certain persons as they relate to producing works of art such as paintings is solved by the art aid devices of the present invention. These include two forms of hollow cylindrical bodies (12, 32) adapted to be releasably connected to a table top (16) adjacent a wheelchair (24) for supporting a work sheet and limiting arm movement, a sheet of material (42) with a slot (43) of a selected shape above a table top supporting a work sheet, and a sheet of material (62) with a slot (63) in which a flanged arm-receiving roller (64) is moved forwardly of a work sheet to guide the arm through a selected but limited range of movement.

8 Claims, 12 Drawing Figures

ART AID DEVICES

TECHNICAL FIELD

This invention relates to devices for aiding persons with physical limitations in creating works of art, particularly paintings.

BACKGROUND ART

It has been found that there are many persons including handicapped, the elderly, children, and the trainably retarded who have below normal motor capabilities in the movement of the arms, wrists and hands but are capable of producing works of art if provided with certain types of mechanical aid devices. Two aspects of art that have been found to be important to handicapped persons are creativity and craftsmanship. Very little known effort has been directed toward providing art aid devices designed to overcome or compensate for different types of motor problems to enable persons having such problems to express both creativity and craftsmanship.

DISCLOSURE OF INVENTION

In accordance with the present invention there are provided several forms of art aid devices which support the drawing in a particular manner in relation to the arms and hands of the person such as a person in a wheelchair and provide limits to arm movement and/or guide the arm through a specific course of travel. These devices enable persons with limitations on and particular types of motor problems to use both creativity and craftsmanship in producing works of art. Embodiments of the present invention shown include two forms of hollow circular bodies open along an end or along a sidewall supporting a work sheet on the inside, a guide slot in a sheet of material above a work sheet, and an arm supporting roller in a guide disposed forwardly of a work sheet.

BRIEF DESCRIPTION OF DRAWINGS

The details of this invention will be described in connection with the accompanying drawings, in which.

DETAILED DESCRIPTION

Figure 1:
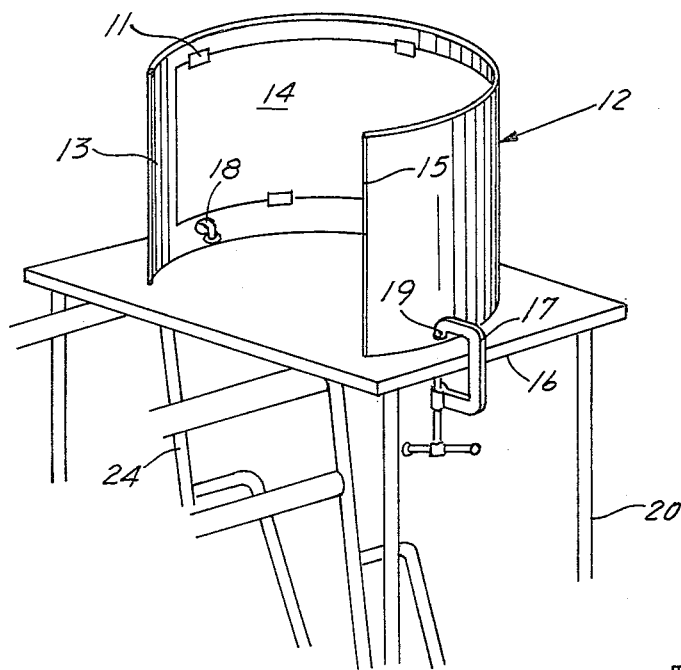
FIG. 1 is a perspective view of an air aid device embodying features of the present invention.
Figure 3:
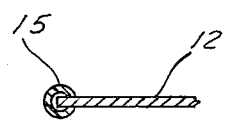
FIG. 3 is a sectional view through the edge of the support member shown in FIG. 1.
Figure 2:
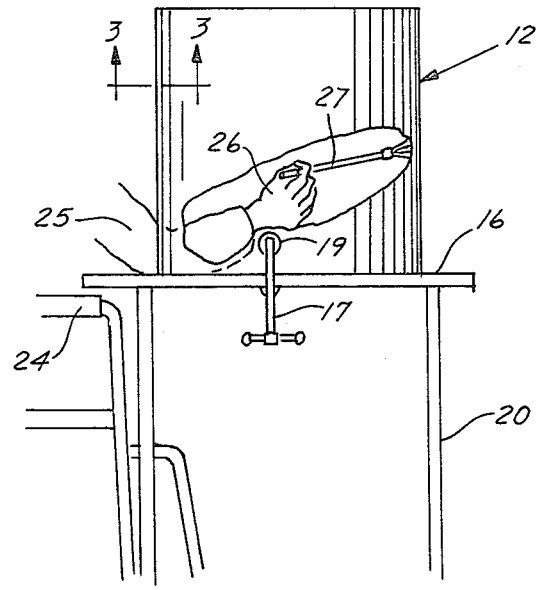
FIG. 2 is a side elevational view of the device shown in FIG. 1 with a wall portion broken away to show the location of the hand and brush.

Referring now to the drawings, in FIGS. 1-3 there is shown an art aid device which includes a support member 12 in the form of a hollow, generally cylindrical body having a smooth, hard, inner surface. This support member 12 is arranged to be disposed upright and is split longitudinally along one side to form an access opening 13 into the inside thereof for receiving the arms and hands of the artist.

An art work sheet 14 of paper or the like is shown secured to the inside surface of the support member as with tape 11. The body is made of a pliable or flexible material with a rigid surface, preferably sheet metal, to give support to the sheet 14 and flex along the slot to permit access as well as change the size of the side opening as required. A sheet plastic material may also be used. Sheet metal may require an enlargement or rounded bead along the exposed edges indicated at 15 to prevent accidental scratching or cutting of the user.

Figure 4:
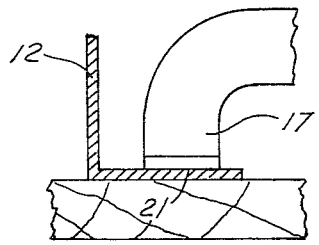
FIG. 4 is a sectional view showing a bottom flange for an alternative form of fastening for the support member shown in FIG. 1.

The support member 12 is shown as having a pair of apertures 18 and 19 formed in the opposite sides and each has a C-clamp 17 that extends through an associated aperture to releasably clamp opposite sides of the member 12 to a table top 16. An alternative construction to the hole is to provide a flange 21 along the bottom edge of the member 12 and the clamps engage this flange, as shown in FIG. 4.

Figure 7:
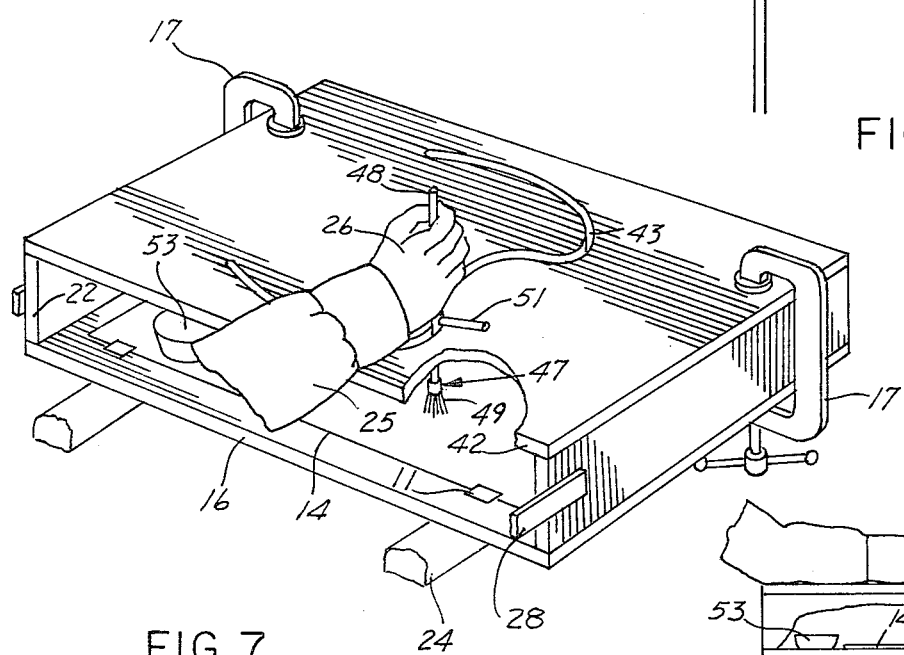
FIG. 7 is a perspective view of another form of art aid device embodying features of the present invention.

A table shown having a top 16 and legs 20 is used as a support for member 12. The height of the legs is appropriate for allowing the arms of the wheelchair to extend under top 16 so that the artist can place the arms 25 on the top with the hands 24 inside the support member 12 as shown. Alternatively, the table top may be of a conventional type frequently provided for wheelchairs that rests on the arms of the wheelchair and has a strap extending around the back of the wheelchair to fasten the table top in place, as is shown in FIG. 7 and discussed hereinafter.

In use, the painter sitting in the wheelchair has the arms 25 supported on the table top and a paint brush 27 or like artist tool in one hand. The painter typically has limited arm movement and limited arm movement control and the table top and support member combine to limit front flopping movements so that the user is able to paint a picture on the sheet. This device provides for smearing, patting and flopping motions.

Figure 5:
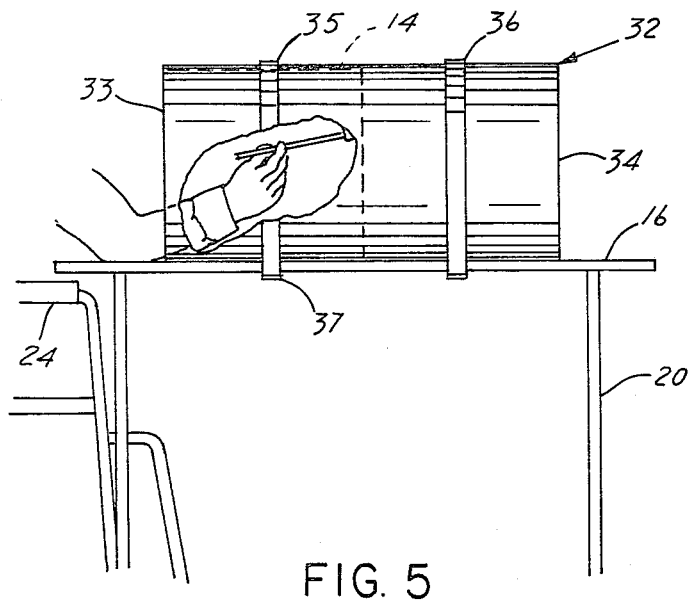
FIG. 5 is a side elevational view of another art aid device similar to that shown in FIG. 1 with a portion of the outer wall broken away to show the position of the brush and hand.
Figure 6:
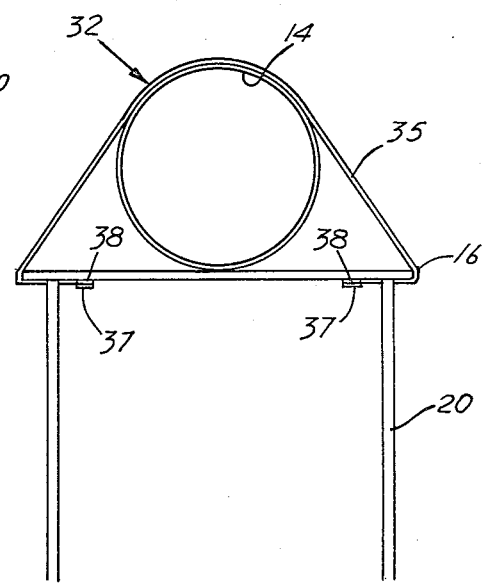
FIG. 6 is a front end view of the device shown in FIG. 5 as viewed from the wheelchair.

Another form of art aid device shown in FIGS. 5 and 6 that is similar to the previously described device comprises a support member 32 in the form of a hollow generally cylindrical body having a smooth hard inner surface that is open at one end to provide the access opening at 33 and may be closed at the opposite end by an end wall 34. The construction and materials may be similar to member 12 above described. An art work sheet 14 is secured to the inside of the support member 32 at the access opening as by tape.

The support member 32 is releasably secured to a table top 16 by a strap assembly shown as including a pair of straps 35 and 36 that extend around the member 32 and have end parts 37 of Velcro or the like that secure to Velcro portions 38 on the underside of the table to releasably secure the straps to the table top.

In using the device shown in FIGS. 5 and 6, the wheelchair is again shown as extending under the table and the arm and hand extend into the open end of the body 32. The painter again has limited arm movement and the device provides for a free flopping arm motion. The device further provides for motor planning, a left-to-right progression, and full exercise of the individual's range of motion.

Figure 8:
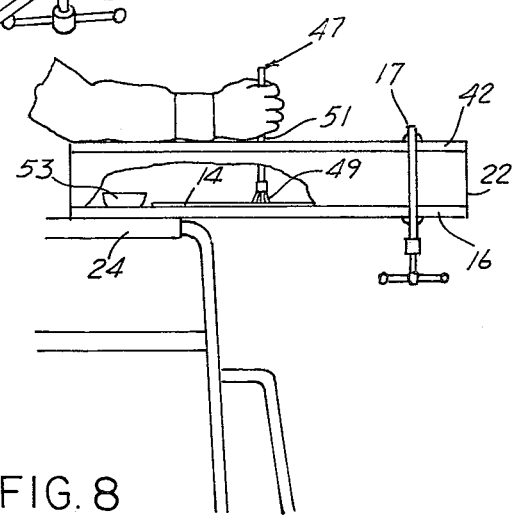
FIG. 8 is a side elevational view of the device shown in FIG. 7 with a wall portion broken away to show interior parts.

Referring now to FIGS. 7 and 8, the art aid device shown has a table top 16 with a work sheet 14 secured thereto. This table top is of the type that mounts on the arms of a wheelchair and has a pair of opposed upright sides 22. Suitable straps 28 are provided to secure the table top to the wheelchair, as is conventional practice.

An upper board 42 of sheet material is releasably mounted on the sides 22 for guiding the hand of the person. This upper sheet of material 42 has a generally sinuous slot 43 formed therein. This slot 43 is arranged as an upright S-shape with an added leg on the top so as to have upper and lower end legs on the left side.

A paint brush 47 shown in FIGS. 7-9 has a hand grip portion 48 opposite the bristle portion 49 and is provided with a transverse rod 51, preferably in the form of a hollow metal rod, that extends through a hole formed in the brush body below the grip portion 48. This transverse rod 51 serves to guide the brush along the top surface of sheet 42 and to prevent the brush from passing through the slot 43 during use. A supply of paint in an open container indicated at 53 is mounted on the table top at one end of the slot 43 to enable the user to conveniently resupply the brush with paint.

In use, the painter seated in a wheelchair uses the hand on the upper sheet of material 42 and grips the grip portion 48 shown. The bristle portion 49 below contacts the sheet and, upon movement of the arm, a work of art is produced by the painter on the art work sheet 14. This device is specifically adapted for persons with limited arm and limited wrist movement and provides for motor planning, left-to-right progression, and an increased range of motion. It is understood that the configuration and arrangement of the slot 43 may vary widely for variations in the art work.

Figure 9:
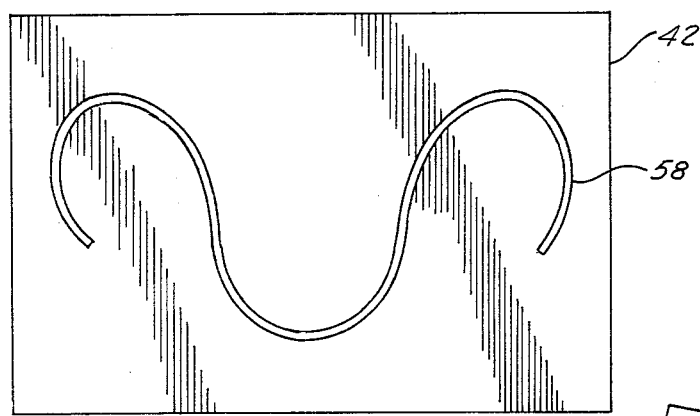
FIG. 9 is a top view of another arrangement for the slot for the sheet material shown in FIG. 7.

Another configuration of slot indicated at 58 is shown in the support member 42 in FIG. 9. This slot is turned so as to have the end legs toward the painter.

Figure 10:
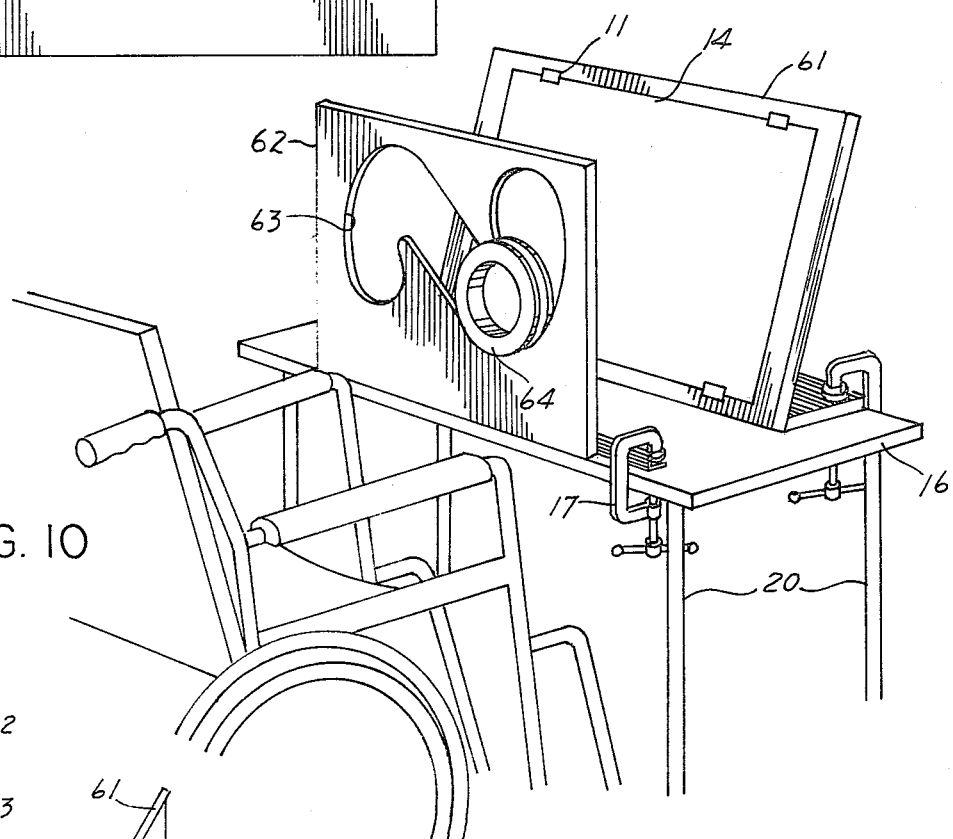
FIG. 10 is a perspective view of another form of art aid device embodying features of the present invention.
Figure 11:
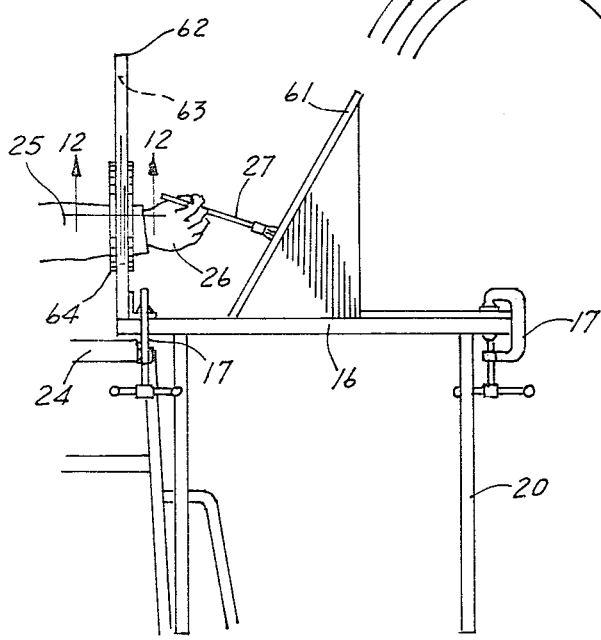
FIG. 11 is a side elevational view of the device shown in FIG. 10.
Figure 12:
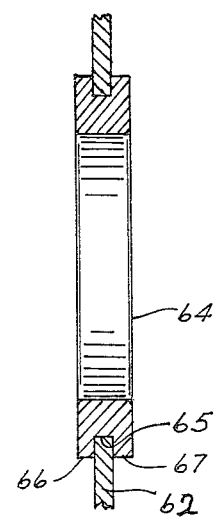
FIG. 12 is a sectional view taken along lines 12—12 of FIG. 11.

In FIGS. 10-12, the art aid device shown includes a conventional easel 61 on which there is secured an art work sheet 14 and a board or sheet of material 62 mounted forwardly of the easel 61. Both the easel 61 and the sheet 62 are releasably clamped to the table top 16 by clamps 17. It is understood that for some applications the easel 61, sheet 62, and table top 16 may be made as an integral unit and eliminate the clamps.

The sheet of material 62 contains a relatively wide curved slot or opening 63 sized to receive and support a hollow or donut-shaped roller 64. The shape of slot 63 may further be characterized as a backward S-shape that is turned rearwardly on its side to a horizontal position which from left to right extends up, down and up in a sinuous pattern. Slot 63 has a substantially uniform width dimension along its length that is slightly greater than the external diameter of the central peripheral surface area 65 of the roller and a width less than the external diameter of the opposed flanges 66 and 67. The roller 64 has a central opening through which the arm extends and has the central peripheral surface area 64 and the opposed flanges 66 and 67 upstanding from surface area 65 arranged so that roller 64 will roll freely in the slot and supported at the top and bottom of the roller by the flanges to guide the arm of the painter in a lateral movement. The roller 64 then tracks on the inner edge of the sheet defining slot 63.

The sheet 62 shown is provided with a bottom flange arranged so that the clamp 17 will clamp this sheet 62 to the table top.

In use, the arm 25 of the painter extends through the opening in the roller 64 and the user, with paint brush 27 in hand, moves the brush against the sheet 14 supported by the easel 61. This device is particularly suited for persons with limited arm movement.

While the wheelchair 24 is shown in a position facing the support sheet of material 62, in many cases it will be turned at right angles thereto to enable the user to more easily extend the arm into the roller.

Although the present invention has been described with a certain degree of particularity, it is understood that the present disclosure has been made by way of example and that changes in details of structure may be made without departing from the spirit thereof.

What is claimed is:

1. In an art aid device, the combination comprising: support means defining a surface area for supporting an art work sheet and for confining arm movement of a person to the sheet whereby the person with physical limitations in arm movement control may create a work of art on said sheet using a paint brush and the like, said support means including a first portion in the form of a hollow, generally cylindrical, pliable, one-piece body having an inner surface of a selected size and shape for supporting said work sheet and limiting flopping-type movements of the arms of the user to said inner surface, said body being disposed upright and having a longitudinal split in one side and spread at the split to provide a variable size arm access opening thereinto, said support means including a second portion below said surface area and means for releasably fastening said body to said second portion.

2. In an art aid device as set forth in claim 1 wherein said body defines a surface area for supporting a work sheet and said second portion guides the arm of a person relative to said work sheet.

3. In an art aid device as set forth in claim 1 wherein said second portion is in the form of a table top.

4. In an art aid device as set forth in claim 1 wherein said means for releasably securing includes at least one C-type clamp.

5. In an art aid device as set forth in claim 1 wherein said body is made of pliable sheet metal with a bead along the exposed edges.

6. In an art aid device, the combination comprising: support means including a first portion in the form of a hollow generally cylindrical body having an inner surface for supporting an art work sheet secured along the inner surface thereof whereby said first portion limits side to side and front flopping movements of the arms of a user that are disposed in said body, and a second portion; and means for releasably securing said first portion to said second portion, said second portion having a substantially horizontal support surface on which the arms of the user are supported whereby a person with limited arm movement and limited arm movement control may create a work of art on said sheet using a paint brush and the like,
said body having an access opening in one end and being disposed on its side in a substantially horizontal position on said support surface.

7. In an art aid device as set forth in claim 6 including strap means to releasably fasten said body to said support surface.

8. In an art aid device as set forth in claim 6 wherein said support surface is disposed adjacent to and extends forwardly of the arm supports of a wheelchair in which the person is seated.

* * * * *